(12) United States Patent
Hemken

(10) Patent No.: US 10,166,680 B2
(45) Date of Patent: Jan. 1, 2019

(54) AUTONOMOUS ROBOT USING DATA CAPTURED FROM A LIVING SUBJECT

(71) Applicant: Heinz Hemken, Foster City, CA (US)

(72) Inventor: Heinz Hemken, Foster City, CA (US)

(*) Notice: Subject to any disclaimer, the term of this patent is extended or adjusted under 35 U.S.C. 154(b) by 179 days.

(21) Appl. No.: 15/224,519

(22) Filed: Jul. 30, 2016

(65) Prior Publication Data

US 2017/0028563 A1 Feb. 2, 2017

Related U.S. Application Data

(63) Continuation-in-part of application No. 14/815,624, filed on Jul. 31, 2015, now Pat. No. 9,676,098.

(51) Int. Cl.
*B25J 11/00* (2006.01)
*B25J 9/16* (2006.01)
(Continued)

(52) U.S. Cl.
CPC .............. *B25J 11/0005* (2013.01); *A61B 5/11* (2013.01); *A61B 5/1121* (2013.01); *A61B 5/45* (2013.01);
(Continued)

(58) Field of Classification Search
CPC ........... A61B 5/11; A61B 5/1121; A61B 5/45; A61B 5/7267; A61B 5/0077;
(Continued)

(56) References Cited

U.S. PATENT DOCUMENTS

| 5,673,367 A | 9/1997 | Buckley |
| 6,070,269 A | 6/2000 | Tardif |

(Continued)

FOREIGN PATENT DOCUMENTS

| EP | 14199382 | 12/2014 |
| WO | WO2004084725 A1 | 10/2004 |
| WO | WO2011107278 A1 | 9/2011 |

OTHER PUBLICATIONS

Automated detection of gait initiation and termination using wearable sensors http://www.robolab.si/fileadmin/user_upload/Publications/publications/2013/novak_ME%26P_13.pdf.
(Continued)

*Primary Examiner* — Lisa Caputo
*Assistant Examiner* — Philip Cotey
(74) *Attorney, Agent, or Firm* — CI II Iabra Law Firm, PC

(57) ABSTRACT

Using various embodiments, an autonomous robot using data captured from a living subject are disclosed. In one embodiment, an autonomous robot is described comprising a robotic skeleton designed similar to that of a human skeleton to simulate similar movements as performed by living subjects. The movements of the robotic skeleton are resultant due to control signals received by effectors present near or on the robotic skeleton. The robot can be configured to receive sensor data transmitted from a sensor apparatus that periodically gathers the sensor data from a living subject. The robot can then process the sensor data to transmit control signals to the effectors to simulate the actions performed by the living subject and perform a predictive analysis to learn the capability of generating spontaneous and adaptive actions, resulting in an autonomous robot that can adapt to its surroundings.

20 Claims, 10 Drawing Sheets

(51) Int. Cl.
*A61B 5/11* (2006.01)
*A61B 5/00* (2006.01)
*B25J 19/02* (2006.01)

(52) U.S. Cl.
CPC ............ *A61B 5/7267* (2013.01); *B25J 9/163* (2013.01); *B25J 19/023* (2013.01); *A61B 5/0077* (2013.01); *A61B 5/6801* (2013.01); *G05B 2219/33277* (2013.01); *G05B 2219/39252* (2013.01); *G05B 2219/40304* (2013.01); *Y10S 901/01* (2013.01); *Y10S 901/46* (2013.01)

(58) Field of Classification Search
CPC ..... A61B 5/6801; B25J 11/0005; B25J 9/163; B25J 19/023; Y10S 901/46; Y10S 901/01; G05B 19/42; G05B 2219/33277; G05B 2219/39252; G05B 2219/40304
See application file for complete search history.

(56) References Cited

U.S. PATENT DOCUMENTS

| | | | |
|---|---|---|---|
| 6,377,281 B1 | 4/2002 | Rosenbluth | |
| 6,754,644 B1* | 6/2004 | Hutchison | G06N 3/08 706/14 |
| 6,834,436 B2 | 12/2004 | Townsend et al. | |
| 7,024,276 B2 | 4/2006 | Ito | |
| 7,657,345 B2* | 2/2010 | Endo | B25J 9/161 318/568.17 |
| 7,664,571 B2 | 2/2010 | Gonzalez-Banos | |
| 7,981,057 B2 | 7/2011 | Stewart | |
| 8,078,321 B2 | 12/2011 | Iba | |
| 8,106,911 B2 | 1/2012 | Gordon | |
| 8,224,652 B2 | 7/2012 | Wang | |
| 8,265,791 B2 | 9/2012 | Song | |
| 8,315,740 B2 | 11/2012 | Hasegawa | |
| 8,347,710 B2 | 1/2013 | Scott et al. | |
| 8,744,627 B2 | 6/2014 | Wieland | |
| 8,751,041 B2 | 6/2014 | Moon | |
| 8,781,624 B2 | 7/2014 | Hodgins | |
| 8,843,236 B2 | 9/2014 | Barajas | |
| 8,925,392 B2 | 1/2015 | Esposito | |
| 8,965,576 B2* | 2/2015 | Chen | B25J 9/0087 700/255 |
| 8,996,167 B2* | 3/2015 | Linder | B25J 9/0087 700/246 |
| 8,996,174 B2* | 3/2015 | Brooks | B25J 9/0087 700/259 |
| 9,266,233 B2 | 2/2016 | Kornbluh | |
| 9,351,900 B2 | 5/2016 | Walsh | |
| 2004/0036437 A1* | 2/2004 | Ito | B25J 9/163 318/568.12 |
| 2004/0162638 A1* | 8/2004 | Solomon | F41H 13/00 700/247 |
| 2007/0233318 A1 | 10/2007 | Lei | |
| 2007/0239641 A1* | 10/2007 | Ito | B25J 9/161 706/23 |
| 2008/0009771 A1 | 1/2008 | Perry | |
| 2010/0249999 A1* | 9/2010 | Glaser | B25J 9/161 700/246 |
| 2013/0040763 A1 | 2/2013 | Davidson | |
| 2013/0054021 A1 | 2/2013 | Murai | |
| 2013/0054028 A1 | 2/2013 | Lee | |
| 2013/0145530 A1 | 6/2013 | Mitra | |
| 2013/0211587 A1 | 8/2013 | Stephens | |
| 2013/0211594 A1 | 8/2013 | Stephens | |
| 2014/0065586 A1 | 3/2014 | Gabbai | |
| 2014/0277718 A1* | 9/2014 | Izhikevich | B25J 9/163 700/250 |
| 2014/0371871 A1 | 12/2014 | Farina | |
| 2014/0371906 A1 | 12/2014 | Barajas | |
| 2014/0371907 A1* | 12/2014 | Passot | G06N 3/008 700/257 |
| 2015/0051734 A1 | 2/2015 | Zheng | |
| 2015/0057984 A1 | 2/2015 | Nicoletti | |
| 2015/0075303 A1 | 3/2015 | Hericks | |
| 2015/0158175 A1 | 6/2015 | Kim | |
| 2015/0196800 A1 | 7/2015 | Macri | |
| 2015/0290795 A1 | 10/2015 | Oleynik | |
| 2016/0059412 A1* | 3/2016 | Oleynik | B25J 9/163 700/257 |

OTHER PUBLICATIONS

Robots that imitate humans https://courses.cs.washington.edu/courses/cse481c/11au/papers/robotsThatImitateHumans.pdf.
Koenemann, Real-time Imitation of Human Whole-Body Motions by Humanoids, URL: http://www2.informatik.uni-freiburg.de/~burgetf/koenemann14icra.pdf.
Billard, Robot learning by demonstration, URL: http://www.scholarpedia.org.article/Robot_learning_by_demonstration.
Liu, Imitation control for biped robot using wearable motion sensor, Journal of Mechanisms and Robotics, v 2, n. 2, p. 1-6, May 2010 URL: http://www.mech.kochi-tech.ac.jp/liutao/ASME-2.pdf.
https://www.xsens.com/company/ (Author unknown).
Teleoperation of a humanoid robot using full-body motion capture, example movements, and machine learning http://www.araa.asn.au/acra/acra2012/papers/pap126.pdf.

* cited by examiner

AUTONOMOUS ROBOT USING DATA CAPTURED FROM A LIVING SUBJECT

CROSS REFERENCE TO RELATED APPLICATIONS

The present application is a continuation-in-part of co-pending U.S. patent application Ser. No. 14/815,624, filed on Jul. 31, 2015, whose contents are incorporated herein by reference in its entirety.

FIELD OF THE INVENTION

Embodiments of the present invention relate generally to the field of autonomous robots. More particularly, embodiments of the invention relate to training of an autonomous robot using data collection captured by a living subject so that the robot can independently provide an expression of human behavior related to the living subject.

BACKGROUND OF THE INVENTION

Robots have been used by mankind to perform relatively simplistic tasks for years. Typically, a robot is programmed to perform the relatively simplistic task (e.g., assembling a portion of a car), by the displacement or movement of a mechanical appendage using a programmable controller. Robots can also be programmed to perform other simplistic tasks like moving, obstacle avoiding, etc.

Autonomous mobile robots can usually require that their functions and behaviors be programmed either explicitly or by means of algorithmic building blocks that, when combined or executed in concert, generate the desired robotic behavior. However, using such contemporary approaches it is difficult to program sophisticated animal-like or human-like behaviors. Thus, what is needed are methods, systems, devices, and apparatuses with which a robot can be trained to become autonomous using data collected by a living subject in a controlled environment.

SUMMARY OF THE DESCRIPTION

Using various embodiments, autonomous robot systems and methods using data captured from a living subject are disclosed. In one embodiment, an autonomous robot is described comprising a robotic skeleton designed similar to that of a human skeleton to simulate similar movements as performed by living subjects. The movements of the robotic skeleton are resultant from control signals received by effectors present near or on the robotic skeleton. The robot, in one embodiment, is coupled to a processing system that can be configured to receive sensor data that is received from a sensor apparatus. In various embodiments, the processing system can reside within the autonomous robot, be coupled to the robot via a local or remote network, or a combination thereof. In one embodiment, the processing system can be a distributed computing system. The sensor apparatus periodically gathers the sensor data from a living subject including at least one sensor to capture the body and limb motions of the living subject, and at least another sensor to capture data related to the surroundings of the living subject, including stereoscopic video and stereophonic audio. In one embodiment, the sensor data also includes the data generated by the sensors. The processing system can further be configured to process the sensor data to transmit control signals to the effectors to simulate the actions performed by the living subject. The processing system can also be configured to perform a predictive analysis to learn the capability of generating actions that are spontaneous and adaptive to the robot's immediate environment, as well as its ongoing interactions with living or inanimate elements that surround it. The data generated from the predictive analysis can then be received and processed iteratively, resulting in spontaneous and adaptive actions by the robot. The robot's control signals are transmitted to the effectors for a next time interval. These signals in one embodiment, can be represented by a conversion function $y=f(x)$, where y represents a vector containing all of the signals that need to be sent to the effectors of the robot, audio generation devices, etc., in the next time interval to make the robot display appropriate behavior, x represents a vector that includes sensor readings that are produced at any given moment by the sensor apparatus, and $f(\ )$ represents a machine learning algorithm function that can receive sensor data and perform computations on the sensor data to yield the appropriate signals to send to the robot's effectors during the next time interval.

In another embodiment, the predictive analysis performed by the processing system of the robot is derived from at least a neural network (primary, secondary, or a combination thereof) that uses layers of non-linear hidden units between its inputs and its outputs. Each unit can then further be assigned a weight during an initial training stage. In yet another embodiment, during the learning stage the robot adapts the weights on the incoming connections of hidden units to learn feature detectors that enable it to predict the correct output when given an input vector.

In another embodiment, the predictive analysis is derived from a first and a second neural network, where the first neural network receives a feed from the sensor data and the second neural network receives a feed related to the immediate surround of the robot. The robotic skeleton can at least be partly formed using universal joint segments.

BRIEF DESCRIPTION OF THE DRAWINGS

The present invention is illustrated by way of example and not limitation in the figures of the accompanying drawings in which like references indicate similar elements.

DETAILED DESCRIPTION

Figure 1:
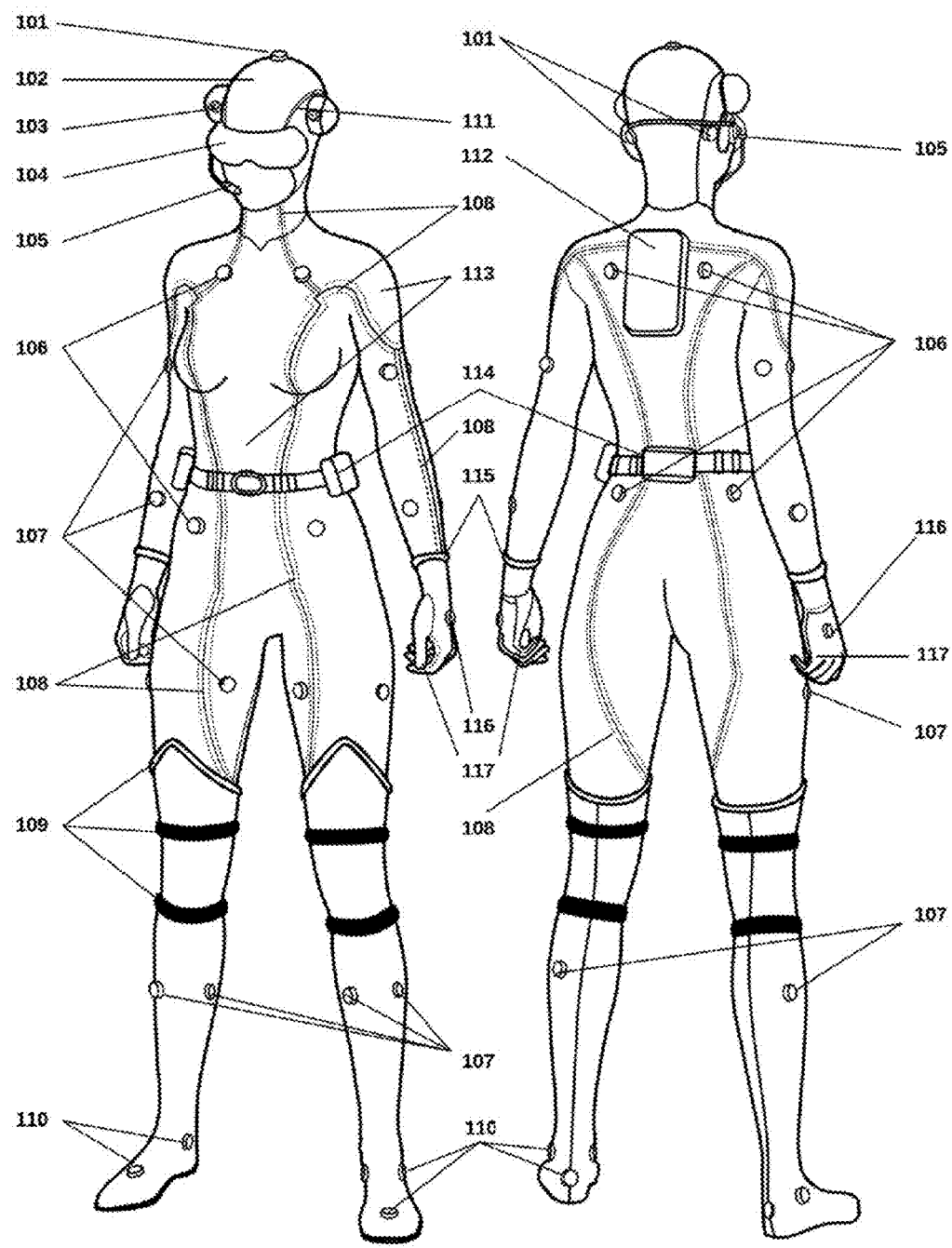
FIG. 1 illustrates diagram 100 depicting a living human subject or autonomous robot wearing a sensor apparatus with sensors using which a robot shaped like the living subject can be trained, according to one embodiment of the present invention.

Various embodiments and aspects of the invention will be described with reference to details discussed below, and the accompanying drawings will illustrate the various embodiments. Reference in the specification to "one embodiment" or "an embodiment" or "another embodiment" means that a particular feature, structure, or characteristic described in conjunction with the embodiment can be included in at least one embodiment of the invention. The appearances of the phrase "in one embodiment" in various places in the specification do not necessarily all refer to the same embodiment. The processes depicted in the figures that follow are performed by processing logic that comprises hardware (e.g., circuitry, dedicated logic, etc.), software, or a combination of both. Although the processes are described below in terms of some sequential operations, it should be appreciated that some of the operations described can be performed in a different order. Moreover, some operations can be performed in parallel rather than sequentially.

In one embodiment, a robot can make use of behavior or action data of a living subject captured by using a sensor apparatus. Various embodiments of a behavior or action data capturing technique from a sensor apparatus are disclosed in co-pending U.S. patent application Ser. No. 14/815,624, and can be employed, in whole or in part, with the present invention. As a result, the above-identified disclosure is incorporated herein by reference in its entirety to the extent that such subject matter is not inconsistent herewith. The behavior/action data captured by a sensor apparatus can be provided for boot-strapping/initial training of the robot such that the resulting autonomous mobile robotic behavior is similar to the behavior exhibited by the living subject wearing the sensor apparatus during the behavior capture sessions. In one embodiment, a machine learning algorithm can be employed to analyze living subject behavior/action data and perform a predictive analysis (also referred to as training a machine learning algorithm, neural network, etc., herein) using which a robot can become autonomously functioning by generating behavior that is spontaneous and adaptive to the moment by moment dynamics of the robot's immediate environment, as well as its ongoing interactions with the living or inanimate elements that surround it. The robot can also recursively perform a predictive analysis on the data generated by its own sensors to further refine its actions, movements, behavior, etc. Therefore, extensive and varied data captured from a living subject would result in more versatile behaviors, movements, actions, etc. that can be generated by the robot.

In a preferred embodiment, an autonomous mobile robot that can display behaviors similar to a living subject can have a body whose shape, movements, degrees of freedom, weight distribution, and outer covering must closely resemble that of the living subject. The robot can possess computational mechanism(s) for such actions/behaviors to be loaded into the system (e.g., from a sensor apparatus) and thereafter those actions/behaviors are displayed by the robot through control signals sent by the computational mechanism to the robot's effectors. In one embodiment, the robot can also capture its own behavior or action data generated by ongoing operation for predictive analysis by a machine learning algorithm to make the robot autonomously functioning. In another embodiment, such a machine learning algorithm can perform a predictive analysis on the data derived from a plurality of living subjects so that more training data is generated to capture more refined or nuanced behaviors exhibited by the living subjects.

Since living subjects often display complex behavior/action/movement patterns while performing a given task, in one embodiment, the living subject is implicit in the behavior capture data itself, permeating it with automatic movements, gaits, skills, habits, gestures, body language, and even spoken language (in the case of humans). In one embodiment, actions and movements related to the above mentioned behavior/actions can be captured by sensor apparatus disclosed in U.S. patent application Ser. No. 14/815,624. Therefore, the structure, ranges of motion, degrees of freedom, mass distribution, and effector dynamics of a robot that are substantially or approximately the same as those of the living subject can be used to process and utilize the data captured from the living subject to produce similar actions by the robot. In one embodiment, the living subject's rich repertoire of behavior can be represented in a machine learning algorithm and used to generate behavior (actions) in the robot that are similar to or, in certain embodiments, indistinguishable from, that of the living subject from whom the behavior data were captured.

In one embodiment, a machine learning algorithm can be trained to be a numerical mapping function to convert the sensor data flowing in from a sensor apparatus into signals needed to cause the effectors of the robot to move its limbs and extremities and to produce vocalizations. The robot can be controlled by transmitting signals in discrete time intervals. In various embodiments, it may be necessary to use tens, hundreds, thousands, or even more time intervals per second to achieve smooth operation. Each successive time interval's set of effector control signals can be determined by gathering a plurality of the most recent consecutive time intervals worth of sensor data being received from a sensor apparatus. In yet another embodiment, the sensor apparatus can also be worn by the robot and supplying the signals to a previously trained machine learning algorithm. Thus control signals transmitted to a robot, in one embodiment, can be represented by a conversion function:

$$y=f(x)$$

Where y is a vector containing all of the signals that need to be sent to the robot's effectors, audio generation devices, etc., in the next time interval to make the robot display appropriate behavior, and x is a vector that includes the sensor readings that are produced at any given moment by the sensor apparatus. Function $f( )$ represents a function that can receive the sensor readings in x, and perform computations on the sensor data to yield y, the appropriate signals to send to the robot's effectors during the next time interval. In one embodiment, $f( )$ can be a machine learning algorithm trained by means of supervised learning with data previously obtained with the sensor apparatus from living subjects, from the robot itself, from a plurality of substantially identical robots, or from a combination thereof. In another embodiment, vector x includes the sensor readings for a plurality of the last most recent time intervals generated by the robotic skeleton.

In one embodiment, a machine learning algorithm, implemented on a computational device, can be trained (that is, perform a predictive analysis) to provide a function $f(\ )$ that can generate predicted values from sensor data generated from a most recent series of consecutive time intervals for which sensor apparatus data are available. Thus, in this embodiment, the robot's actions within the next fraction of a second can be defined by what the robot had been doing for the past several time intervals (e.g., seconds, minutes, and/or hours). In one embodiment, the number of time intervals per second needed to achieve smooth and acceptable operation will vary according to specific applications and can depend on the computing and communications capabilities of the materials and devices used to construct the robot, as well as the number, type, location and organization of the sensors in the sensor apparatus. In one embodiment, it may be necessary to use tens, hundreds, or thousands of time intervals of sensor data to compute each succeeding time interval's worth of robot control signals.

In one embodiment, the machine learning algorithm is a feed-forward, artificial neural network (ANN) that uses layers of non-linear "hidden" units between its inputs and its outputs. Such ANNs are often referred to as Multi-Layer Perceptrons (MLPs). Each unit has a weight that is determined during learning, which can be referred to as a training stage. In the training stage (that is, prior to performing a predictive analysis), a training set of data (a training set of inputs each having a known output) is processed by the neural network. Thus, it is intended that the neural network learns how to provide an output for new input data by generalizing the information it learns in the training stage from the training data. Generally, once learning is complete, a validation set is processed by the neural network to validate the results of learning. Finally, test data (i.e., data for which generating an output is desired) can be processed by a validated neural network. The purpose of learning is to adapt the weights on the incoming connections of hidden units to learn feature detectors that enable it to predict the correct output when given an input vector. In another embodiment, variations of ANNs, as known to a person of ordinary skill in the art may be used. For example, in one embodiment, a Recurrent Neural Network (RNN), which are models with bi-directional data flow, can be implemented. A person having ordinary skill in the art would appreciate that while a feed-forward ANN propagates data linearly from input to output, RNNs also propagate data from later processing stages to earlier stages. Thus, RNNs can be used as general sequence processors, and are often used for time-series data. In yet another embodiment, a combination of ANNs and RNNs can be used.

The skeletal structure of the robot, in one embodiment, can be designed similar to that of a human skeleton in which the joints that operate essentially as hinges are replaced with either a variation of a universal joint or with hinge-like linkages, and those with greater degrees of freedom than a mere hinge are replaced with a variation of a universal joint. The natural anchor points where muscles or tendons are attached to the skeleton of a living subject are used as anchor points for the effectors that can be used to perform the same functionality of muscles of a living subject, in order to closely approximate the force vectors acting on the skeleton of the living subject as a result of muscle contraction and relaxation.

In one embodiment, the muscle groups that provide force vectors on the living subject's skeleton to cause characteristic movements are replaced in the robot by effector mechanisms such as electric motors of various types, pneumatic or hydraulic pistons, or any other means of supplying force, without departing from the scope of the present invention, to pull or push skeletal elements in the proper direction. Said effectors can be attached directly to the skeletal elements or indirectly by means of gears, pulleys, cables, chains, bands, flywheels, springs, screws, or any other mechanical linkage, without departing from the scope of the present invention. In concert, the effectors and their mechanical linkages to the skeleton result in characteristic movements of the robot skeleton that are approximately the same as those of the corresponding skeletal region of the living subject. Actual effector mechanisms, such as electric motors of various types, pneumatic or hydraulic pistons, gears, pulleys, mechanical and electrical cables, chains, bands, flywheels, springs, batteries, electrical and electronic circuits and components, wiring, micro-controllers, computer systems, computer storage systems, computer networking components, etc. can be placed in locations that aid in proper distribution of mass throughout the robot's body. In one embodiment, the actual effector mechanisms can be attached to limb bones or within larger cavities such as the robot equivalents of torso, abdomen, head, or buttocks.

In yet another embodiment, the robot body with a skeleton closely mimicking the degrees of freedom of a living subject's skeleton, with effector mechanisms suitably mounted within, can be fitted with an outer covering analogous to the skin surface of a living subject with approximately the same compressibility, flexibility, shape change, etc. as the skin of the living subject. In one embodiment, this can be the final outer covering over any and all ribbing, casings, effector mechanism coverings, elastomer foam, flexible or inflexible structural components, etc. that ultimately results in an outer form approximately the same as that of the living subject's skin. In one embodiment, a sensor apparatus can fit over the robot's outer covering in a similar manner as when worn by a living subject. In yet another embodiment, the robot's skeleton can be composed of parts that provide a skeletal structure whose degrees of freedom, range and limitations of movement, size, and proportion are approximately the same as those of the living subject's skeleton, but which have been shaped and manufactured in a manner and from materials that facilitate the mounting of the mechanical, electrical, and electronic parts needed for the proper functioning of the robot. The individual parts may be very different from the corresponding parts of the living subject's skeleton, but they provide approximately the same functional and dynamic properties and characteristics.

In an embodiment, the skeletal structure of the robot and the array of effectors mounted therein are capable of closely mimicking the movements of a living subject's body over its entire range of movements when provided with suitable effector control signals. This assembly is fully enclosed by a material that reproduces the overall shape and mechanical feel of the living subject's body surface accurately enough that a sensor apparatus fits over it in the same way and just as snugly and as on a living subject. In this embodiment, the motions and shape changes of the robot are indistinguishable from those of the living subject as measured by the sensor readings of the sensor apparatus (also referred to herein as a behavior capture suit). For a corresponding movement, series of movements, or set of concerted movements, the robot body and the living subject's body generate substantially the same sensor signals in the sensor apparatus.

Therefore, a generic platform is disclosed herein that closely parallels the structure of the living subject to train a robot to perform similar actions, behavior, tasks, and movements as those of a living subject. The robot does not need to be programmed explicitly with any kind of robot motion and trajectory control system, image or audio analysis system, language processing system, or task planning and execution system. If behaviors are present in the training data used to train the machine learning algorithm, they will be expressed by the machine learning algorithm through the robot's body.

The following description and drawings are illustrative of the invention and are not to be construed as limiting the invention. Numerous specific details are described to provide a thorough understanding of various embodiments of the present invention. However, in certain instances, well-known or conventional details are not described in order to provide a concise discussion of embodiments of the present invention.

FIG. 1 illustrates diagram 100 depicting a living human subject or an autonomous robot wearing a sensor apparatus with sensors using which a robot shaped like the living subject can be trained, according to one embodiment of the present invention. In one embodiment, the sensor apparatus can be in the form of a garment usable for capturing and recording the behavior of a living human subject, or of an autonomous mobile human-shaped robot, as disclosed in U.S. patent application Ser. No. 14/815,624. The sensor pods described can include but are not limited to multi-axis acceleration sensors each capable of detecting at its mounting point the tilt, orientation, and motion including static acceleration of gravity as well as dynamic acceleration resulting from motion, shock, or vibration, as well as proximity sensors, bend sensors, pressure sensors, temperature, humidity, barometric pressure sensors, radiation detectors, multi-spectral video, subsonic or ultrasonic sound sensors, etc. In one embodiment, sensor pods 101 can be coupled to a headpiece of the covering material to capture head movement, rotation, or orientation. In another embodiment, the covering material of the headpiece can be coupled or embedded with pressure, bend, stretch, proximity, or other sensors in the headpiece material 102 of the covering material. In one embodiment, the headpiece pod 103 can be coupled with video and/or audio capture devices as well as other sensors. In another embodiment, goggles 104 can be used by living subject to view video captured by headpiece video cameras during sensor data capture sessions. In yet another embodiment, headset 105 (with microphone or any audio capturing device) can be used to capture vocalizations made by living subject and headphones to provide audio feedback from selected sensors, or microphones.

In another embodiment, sensor pods 106 can be coupled to any major body region to capture the region's movement, rotation, orientation, etc. Similarly, in another embodiment, sensor pods 107 can be coupled or connected to the limbs and extremities to capture their movement, rotation, orientation, etc. In one embodiment, seams 108 in the covering material can be introduced for size adjustment and for embedding sensors, electrical conductors, communications cables, etc. As illustrated, in one embodiment, thickened regions 109 of the covering material can be created where larger devices, sensors, cables, etc. may be embedded into the thickened regions 109. In one embodiment, sensor pods 110 on footwear can capture their movement, rotation, orientation, external object proximity, etc. In one embodiment, seams 111 in the headpiece of the covering material can be introduced for size adjustment and for embedding sensors, electrical conductors, communications cables, etc. Further, in one embodiment, the sensor apparatus garment can also have at least one of attached fixtures 112 to include computer systems, storage systems, battery systems, or any larger devices that cannot be conveniently embedded in the material of the garment itself.

In another embodiment covering material 113 of the sensor apparatus can comprise pressure, bend, stretch, proximity, or other sensors embedded in the garment material. In yet another embodiment, the sensor apparatus can have at least one fixture 114 to contain computer systems, storage systems, battery systems, or any smaller devices that cannot be conveniently embedded in the material of the garment itself attached to at least one of belts or harnesses. In another embodiment, thickened regions 115 can be introduced at hand-pieces where devices, sensors, cables, etc. can be embedded. Sensor pods 116, in another embodiment, on the hand-pieces can be placed to capture the movement, rotation, orientation, external object proximity, etc. of the hands. In yet another embodiment, sensors on finger or gripper regions 117 can be placed to detect grasping force and other measurements when the hand-piece manipulates objects.

In one embodiment, the living subject wears the sensor apparatus described herein, and as the living subject moves and speaks, a data processing unit of the sensor apparatus can periodically capture and store at least one objective measurement of the living subject's motions and movements, changes in posture, changes in position, vocalizations, gestures, grasping, gait, or other bodily dynamics, as well as real-time video and audio of what is occurring around and in front of the living subject. In one embodiment, the data processing unit of the sensor apparatus can store the data generated by the sensors to a storage medium, in a format that can be retrieved and processed by another computing device, for use by an autonomous robot such that the autonomous robot can exhibit approximately the same movement or action exhibited by the living subject while the data was being captured.

As illustrated in FIG. 1, the form of an autonomous mobile human-shaped robot uses the same or an identical garment as its outer covering. With the exception of the exposed areas of the human subject not covered by the garment, the human wearing the garment and the corresponding robot can be visually indistinguishable. Therefore, a single illustration is shown to represent both the human living subject and the autonomous robot. The robot's physical structure, as illustrated herein, is further required to have the same degrees of freedom in its trunk, limbs, and other major body parts as the living human subject. The degrees of freedom of the robot's hand and finger motion may be equal to or less than that of the corresponding human subject.

As the living subject moves and speaks, the sensor apparatus can capture a plurality of objective measurements of the living subject's movements and vocalizations, as well as real-time video and audio of what is occurring around and in front of the living subject. The sensor apparatus can be configured to capture information needed to determine the moment to moment movement, vocalizations, and activities of an autonomous mobile robot immersed in a work environment similar to that of the human subject.

Figure 2:
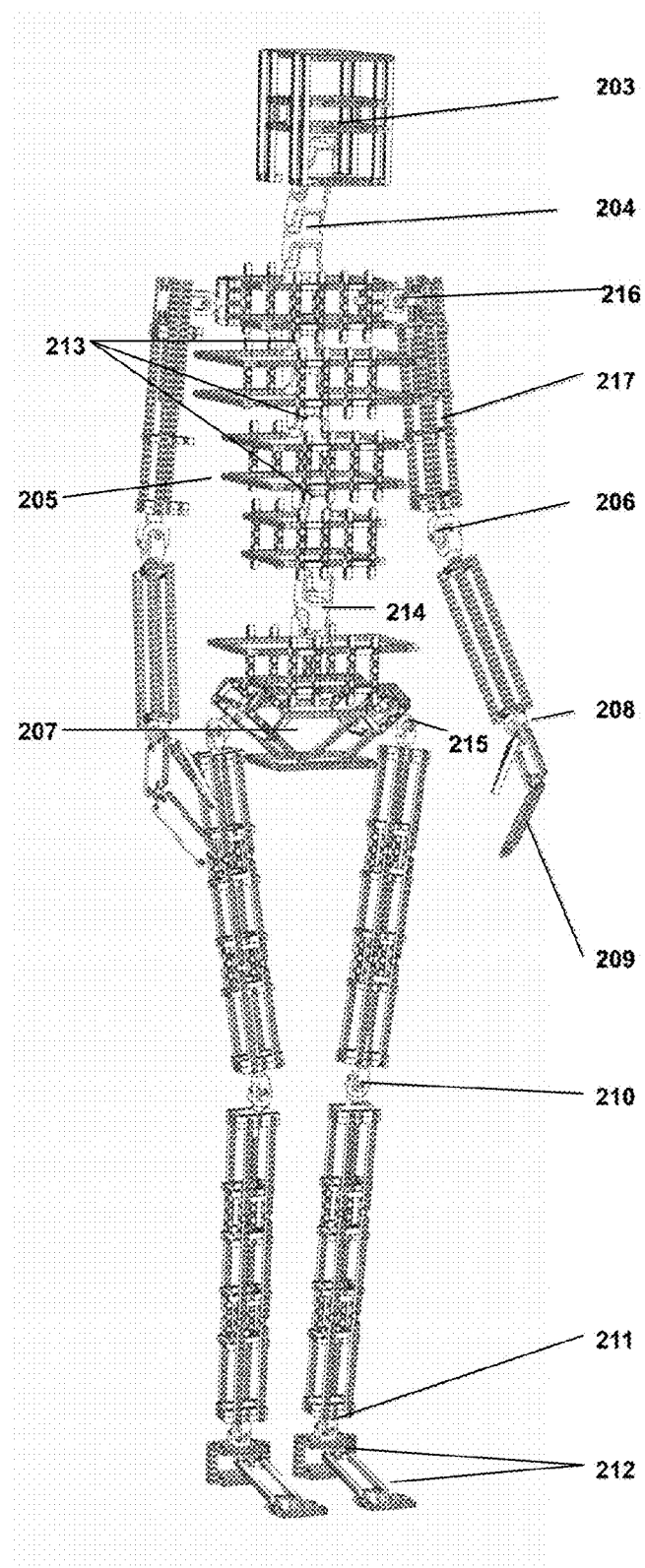
FIG. 2 illustrates a diagram of a robotic skeleton having approximately the same freedom of motion as a human skeleton to effectively imitate any movement performed by a human living subject, according to one embodiment of the present invention.

FIG. 2 illustrates a diagram of a robotic skeleton having approximately the same freedom of motion as a human skeleton to effectively imitate any movement performed by a human living subject, according to one embodiment of the present invention. As illustrated, skeleton 202, in one embodiment, describes a robotic skeleton for an autonomous mobile human-shaped robot using standardized construction elements. As illustrated, head 203 is mounted on flexible stand 204 for the cervical region of the spinal column composed of universal joint segments made of any composition or material known to a person of ordinary skill in the art. The region analogous to a human spinal column is illustrated as a stand structure 205 for the torso region of the skeleton where shelving and other structural units can be used to attach effectors, computing equipment, networking and communications equipment, batteries or other power supplying mechanisms, or any other physical devices as needed. Subsections of the torso can be connected to each other by additional 213 universal joint segments. The upper structure 217 of the arm is attached to the torso section by means of a universal joint 216. Elbow joint 206 can also be a universal joint whereas wrist 208 is, in one embodiment, represented as a hinge, to which gripper 209 is attached in turn. The torso section can be connected by another flexible stand structure 214 analogous to the lumbar spinal column in humans. Stand structure 214, in one embodiment, is composed of universal joint segments, and coupled to a pelvic section 207. In one embodiment, pelvic section 207 also provides amenities to provide shelving, anchor points, and any other needed structural elements. This section has mounting points for, among other structures, universal joints 215 that attach the upper end of the leg to the pelvic region. Knee joint 210 and ankle joint 211 are universal joints, whereas foot articulations 212 are hinges.

Figure 3:
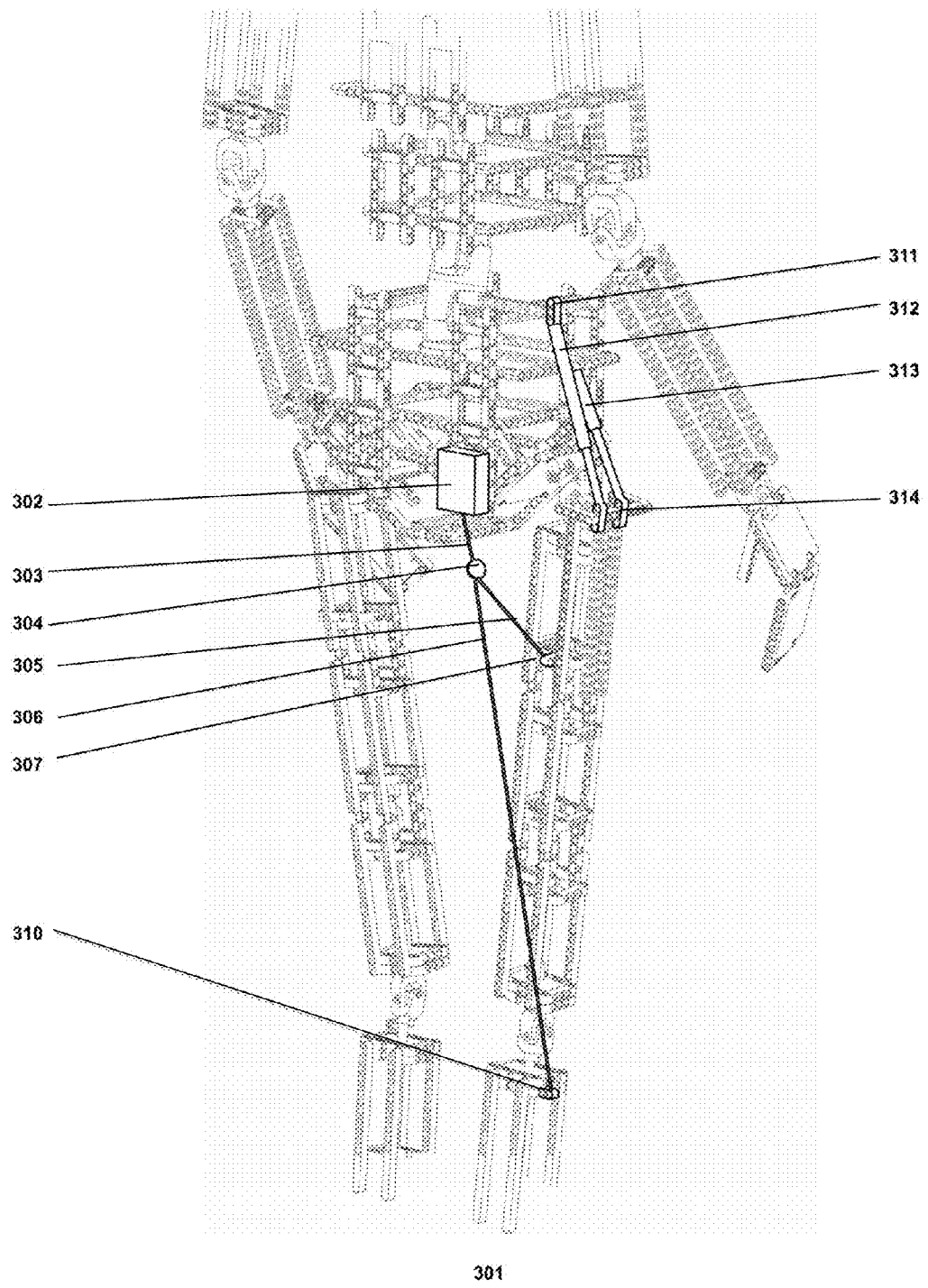
FIG. 3 illustrates a close-up rendering of a robotic skeleton depicting effectors that can be mounted to imitate natural human movements, according to one embodiment of the present invention.

FIG. 3 illustrates a close-up rendering of a robotic skeleton depicting effectors that can be mounted to imitate natural human movements, according to one embodiment of the present invention. FIG. 3 illustrates the mounting of the effectors with the goal of duplicating natural human movements of the hip region 301, as seen from the rear. Generally, in humans, numerous muscles are attached at various points on the skeleton. However, for exemplary purposes, only three muscles are illustrated in bold lines against finer lines representing the rest of the skeleton. In one embodiment, attachment point 311 simulates the crest of the pelvis where the gluteus medius muscle is attached in humans. The muscle is replaced in the robot by pneumatic or hydraulic actuator 312, which is also attached to the upper leg at 314. In one embodiment pneumatic or hydraulic actuator 313 can be configured to represent the gluteus minimus muscle, a muscle that attaches to a more central region of the pelvis in humans. Pneumatic or hydraulic actuator 313 can further be anchored at attachment point 314. In mammals, many larger muscles have wide attachment points, and these can be replaced by mechanisms with branched attachments. A cable-pulling mechanism 302 (comprising gears, pulleys, spools or other parts commonly known to those skilled in the art) can be configured to draw cable 303 which in turn can be attached to ring 304 or other connector to which a plurality of cables 305 and 306 can be attached. These can be anchored to separate distal points 307 and 310. However, since a cable pulling system cannot push back, thus, the above disclosed system would need other actuators/effectors (not shown) to pull the robotic skeletal element back in the opposite direction.

Figure 4A:
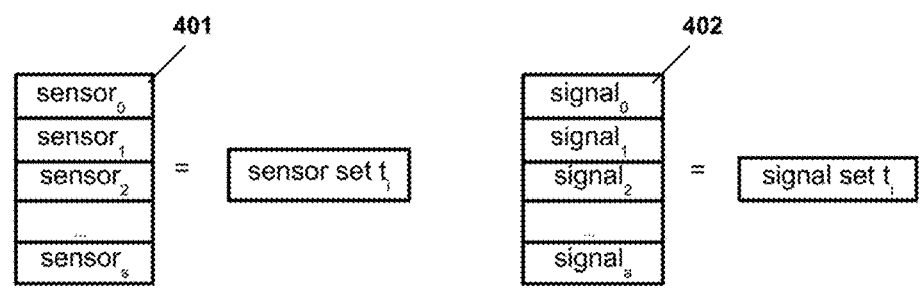
FIGS. 4A and 4B illustrate sensor data of a sensor system, according to one embodiment of the present invention.

FIG. 4A illustrates the organization of the data captured from living subjects and how it is used to train a machine-learning computer program. In FIG. 4A, at any given time point i, the sensor system yields s sensor readings, where s is the total number of sensors, audio and video capture devices, etc. comprising the system. All of the data from the sensor system at time point i ($t_i$) can be represented by sensor set $t_1$, 401 Likewise, all of the number a actuator signals needed for the robot to perform all of its operations during a given time point i can be represented by signal set $t_i$, 402.

Figure 4B:
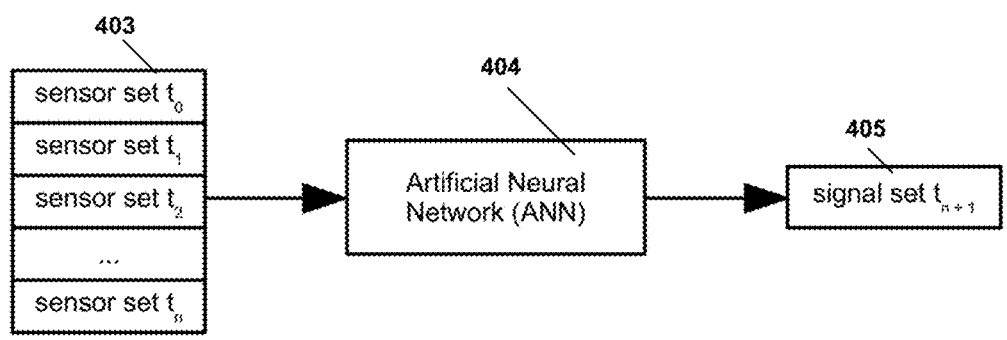

FIG. 4B illustrates a diagram depicting the data processing by an artificial neural network (ANN) of an autonomous robot. The robot's ANN 404 receives as input a full set of sensor system data 403 for each of the last n time points. It outputs the set of a signals 405 needed to actuate all of the number a of the robot's motion generating mechanisms and communications outputs during the next single time interval, time point n+1 ($t_{n+1}$), as further shown in FIG. 5.

Figure 5:
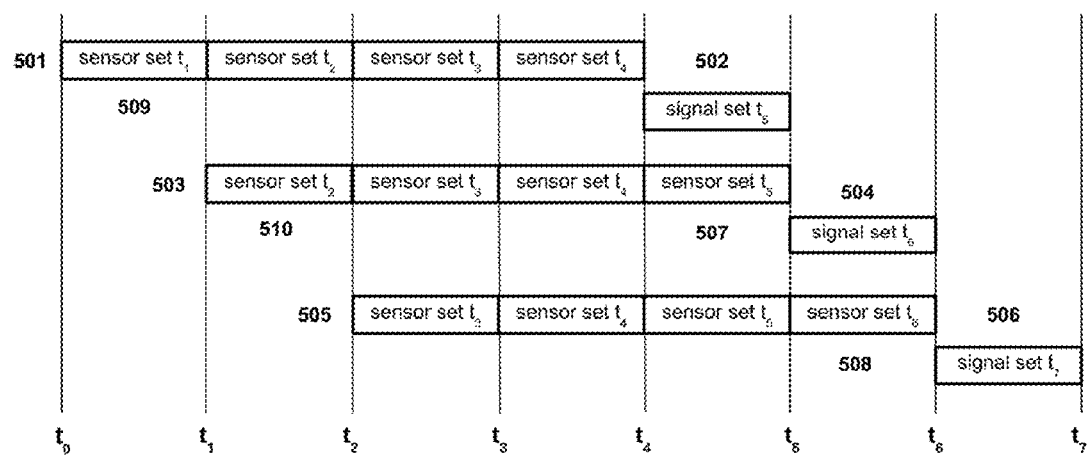
FIG. 5 illustrates a diagram of data that can be input to and output from the machine learning program or algorithm on consecutive time intervals, according to one embodiment of the present invention.

FIG. 5 illustrates a diagram of data that can be input to and output from the machine learning program or algorithm on consecutive time intervals, according to one embodiment of the present invention. In 501, after the first n time points of sensor data have been accumulated, the machine-learning program can compute the first single time point's worth of robot control signals 502. In this schematic example, n=4. Therefore, after the sensor data has accumulated at least 4 time points, they are used to compute the control signals for time point 5, signal set $t_5$ 502. This signal set is sent to the robot's motion and audio generating system to execute its activities during the next time increment, as well as to the robot's data storage mechanism. In 503, after time point 5 ($t_5$) has elapsed, a new time point's worth of sensor data has been accumulated, sensor set $t_5$ 507, which reflects the movement of the robot as well as the new video, audio, and other data captured from the environment over that time interval. The sensor data from the first time point $t_1$ 509 are now more than n=4 time points away in the past, so they are discarded as inputs to the machine-learning program (although they are still saved in the sensor system's data storage mechanism). Now only the 4 time points $t_2$ through $t_5$ are used to compute the control signals for the next time point, $t_6$ 504.

In 505, as in 503, another time interval has elapsed and another set of sensor data has been accumulated, sensor set $t_6$ 508. Now the oldest previous set of sensor data is discarded 510, and the sensor data from time points $t_3$ through $t_6$ are used to compute the next time interval of control signals, signal set $t_7$ 506. The above mentioned process can be done continuously during the entire time the robot is in operation. In the example, the number of time intervals used to calculate each time point's worth of robot control signals was 4. In practice, this is likely to be substantially more. It may be necessary to use tens, hundreds, thousands, or even more time intervals to compute each succeeding time point's worth of robot control signals. The number of time intervals per second needed to achieve smooth and acceptable operation will also vary according to specific applications and will depend on the computing and communications capabilities of the materials and devices used to construct the robot, as well as the number, type, location and organization of the sensors in the sensor system without departing from the scope of the present invention.

Figure 6:
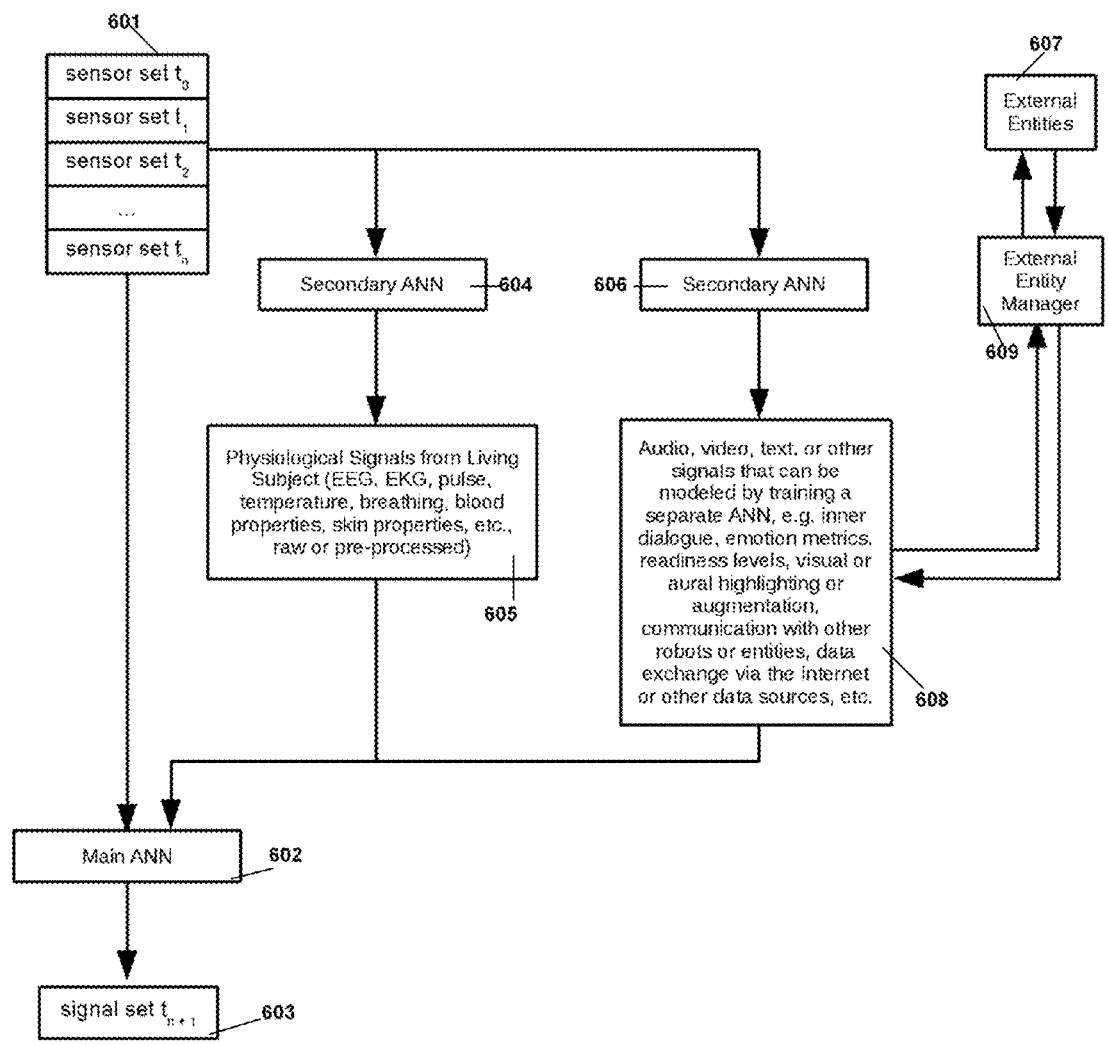
FIG. 6 illustrates a secondary Artificial Neural Network (ANN) that can be used to model or simulate inputs to a primary ANN that generates the effector signals to drive the robot, according to one embodiment of the present invention.

FIG. 6 illustrates the use of Artificial Neural Networks (ANNs) to generate the effector signals to drive the robot, according to one embodiment of the present invention. In one embodiment, the machine learning algorithm is a feed-forward, artificial neural network (ANN) that uses layers of non-linear "hidden" units between its inputs and its outputs. Such ANNs are often referred to as Multi-Layer Perceptrons (MLPs). Each unit has a weight that is determined during learning, which can be referred to as a training stage. In the training stage, a training set of data (a training set of inputs each having a known output) is processed by the neural network. Thus, it is intended that the neural network learn how to provide an output for new input data by generalizing the information it learns in the training stage from the training data. Generally, once learning is complete, a validation set is processed by the neural network to validate the results of learning. Finally, test data (i.e., data for which generating an output is desired) can be processed by a validated neural network. The purpose of learning is to adapt the weights on the incoming connections of hidden units to learn feature detectors that enable it to predict the correct output when given an input vector. In another embodiment, variations of ANNs, as known to a person of ordinary skill in the art may be used. For example, in one embodiment, a Recurrent Neural Network (RNN), which are models with bi-directional data flow can be implemented. A person having ordinary skill in the art would appreciate that while a feed-forward ANN propagates data linearly from input to output, RNNs also propagate data from later processing stages to earlier stages. Thus, RNNs can be used as general sequence processors, and are often used for time-series data. In yet another embodiment, a combination of ANNs and RNNs can be used.

FIG. 6 depicts a plurality of ANNs. As illustrated, secondary ANNs 604 and 606 can be used, in an embodiment, to model or simulate additional inputs to the primary (main) ANN 602 that generates the effector signals 603 to drive the robot in addition to the sensor sets 601. In one embodiment, the secondary ANNs can be used to model dynamics that are present in the living subject, such as electrocardiography (EKG), electroencephalography (EEG), or respiratory measurements 605. Secondary ANNs can also be used to model complementary information 608 that is added to the training data after the behavior/action capture session of a living subject wearing the sensor apparatus, such as additional imagery or audio developed and curated by the robot-training technical staff, with enough structure and consistency that an ANN can be trained to provide it autonomously later in the robot.

Secondary ANNs, in one embodiment, can also be used to upload and download data through an external entity manager 609 to external entities 607, e.g. via the Internet or other data sources, with the data received injected into primary/main ANN 602. In each of these cases secondary ANNs 604 and 606 can be trained separately from main ANN 602. In one embodiment, during training, secondary ANN 604 receives data from the sensor apparatus as disclosed in U.S. patent application Ser. No. 14/815,624. The output data it is trained to reproduce are derived from sensors placed on the living subject separately from said sensor apparatus, such as EKG or EEG measurement devices. These devices are not part of the sensor apparatus because the robot cannot provide EKG or EEG signals. Therefore, in order to simulate such signals, secondary ANN 604 can be used to generate EKG or EEG signals based on the sensor signals being received from the sensor apparatus. The simulated EKG or EEG signals are then fed into main ANN 602. These EKG and EEG signals encode some aspect of the living subject's subjective emotional state. By using these signals the robot can be configured to express emotional nuance in its behavior similar to that of the living subject. Such emotional overtones can be useful to facilitate rapport between a human-shaped autonomous mobile robot and human collaborators or clients.

In another embodiment, at least another other secondary ANNs 606 can be used to provide signals that are not generated by a sensor apparatus or from a living subject, and then used to feed inputs into main ANN 602. In one embodiment secondary ANN 606 can be used to provide complementary audio, video, text, or other data that can be determined necessary for the robot's ongoing behavior. As an example, this may include, without limitation, audio and video reminders to stay on tasks until the task(s) is finished, information related to elements in the surrounding environment (augmented reality), or any other material that is deemed useful or desirable to complement the autonomous mobile robot's other data inputs. In one embodiment, such signals can be a mechanism to deliberately guide the robot's behavior using information compiled and curated at the time of training data creation.

In one embodiment, the functionality of secondary ANNs 604 and/or 606 can be performed by primary/main ANN 602. In another embodiment, regardless of the presence or absence of secondary ANN 604 and/or secondary ANN 606, both the information gathered from motion sensors in the sensor apparatus as well as data from audio and video capture devices in the sensor apparatus can be inextricably mixed in ANN 602. In one embodiment, a single all-encompassing ANN controls all of the robot effectors at once. In another embodiment, since audio and video data can include far more raw data than do even significant numbers of motion capture devices, the audio and video data can have a higher weight assigned in the ANN than do the motion capture devices. Since the audio and video data are derived from the surroundings of the living subject or of the robot, the training data and therefore the behavior of the robot are determined in far greater measure by what can be occurring in the space surrounding the sensor apparatus than by the mechanical movements it is capturing from the living subject's or the robot's body. The motion data, in one embodiment, is complementary to the environmental data. By combining motion and environmental data, in one embodiment, the system can use both inward facing and outward facing sources of dynamic sensor data to determine the behavior of the autonomous mobile robot. This intimate combination of body-centric and environment-centric data forms the basis for the emergence of intelligent-seeming behavior. Data that determine the production of the motion, when the motions should cease, and how it should change with time due to changes in the environment are richly represented in the multi-modal data coming in from the sensor apparatus.

In yet another embodiment, by feeding the outputs of additional specialized secondary ANNs, the multi-modality of the input data can further be increased to generate refined intelligent behavior or actions by the robot. Thus, including physiological data reflecting emotion and alertness in the living subject, as illustrated at block 605, provides subtle behavioral clues that are entirely absent in the motion detector, audio, or video data. Including even more multi-modal data consisting of more images, video, verbal commentary, task-focused reminders, highlighting elements in the visual field, and other carefully curated data as simulated in a separately trained ANN, as illustrated at 608, can add greater information to guide complex behaviors in an autonomous mobile robot. Further, training a secondary ANN to constantly consult one or a plurality of external data sources, as illustrated at 609, can allow the robot to send and receive data to resolve problems and ambiguities in real time. In particular issues can be addressed and resolved that are not already trained into its other ANNs but that have already been addressed by external entities such as the robot's manufacturer, its owner or operator, or any of a variety of public or private data services that can be set up for this purpose.

Figure 7:
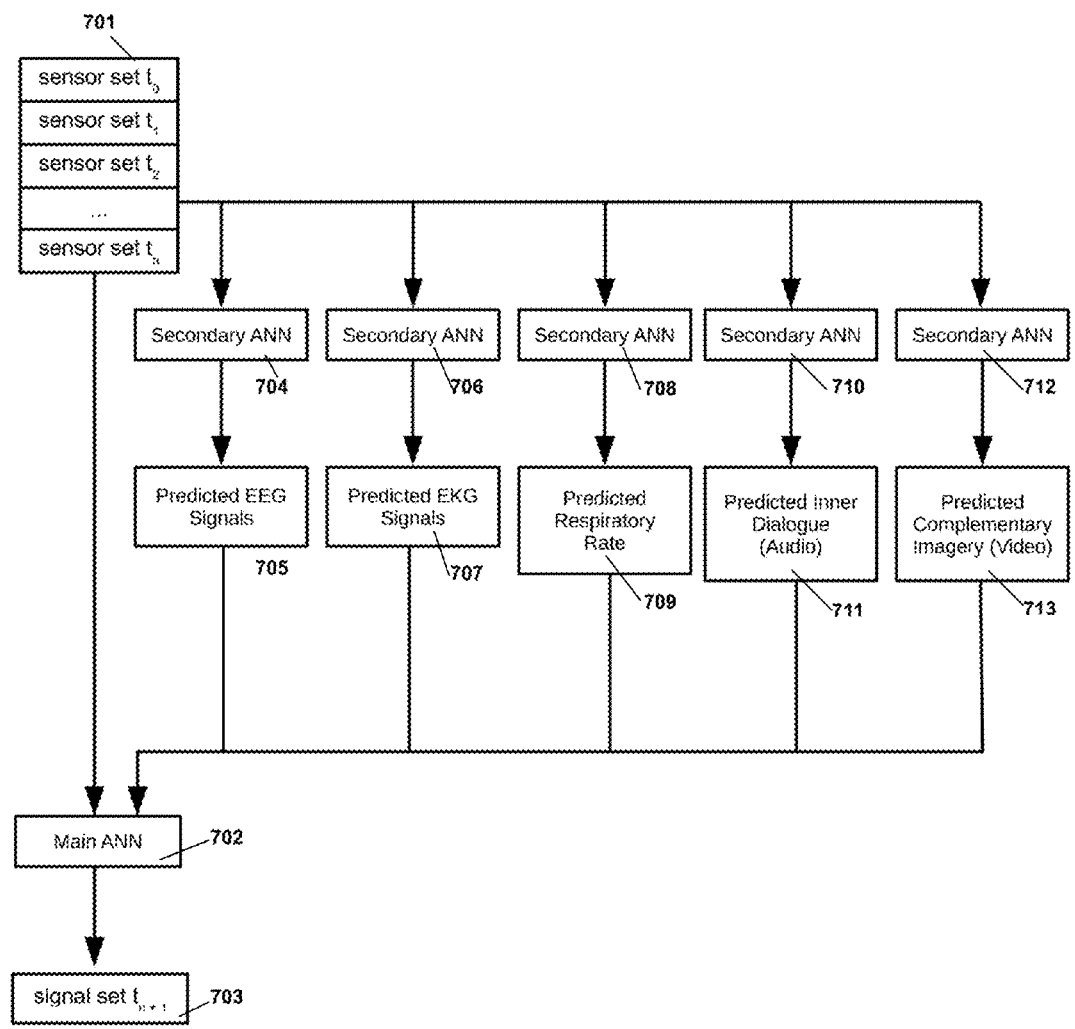
FIG. 7 illustrates a robotic training system using a secondary ANN, according to one embodiment of the present invention.

FIG. 7 illustrates robotic training system using a plurality of secondary ANNs, according to one embodiment of the present invention. In one embodiment, sensor signals 701 can be received from a sensor apparatus, as disclosed herein. As illustrated, five secondary ANNs 704, 706, 708, 710, and 712 can be trained to simulate EEG, EKG, respiratory rate, a human-defined audio track named "inner dialogue," and a human-defined track of complementary still or video data, respectively. Along with data from the sensor apparatus, these secondary ANNs also feed their outputs into the main ANN 702. In this embodiment, the autonomous mobile robot has its behavior, as expressed in the outgoing signal set 703, determined by the surrounding environmental and proprioceptive data received from the sensor apparatus; the emotional state information reflected in the living subject's EKG, EEG, and respiratory dynamics; and/or a parallel internal multimedia realm in which the robot designers can inject complementary data they deem is useful to maintain acceptable ongoing behavioral and task completion dynamics in the robot. Since these data are stored by the robot (as further illustrated in FIG. 8), in one embodiment, it is possible to view and listen to what an autonomous robot has been generating in those internal multimedia tracks either live as they are being generated or afterwards. In one embodiment, such detailed auditable data can help an operator, manufacturer or administrator of the robot understand the robot's behavior on specific occasions.

Figure 8:
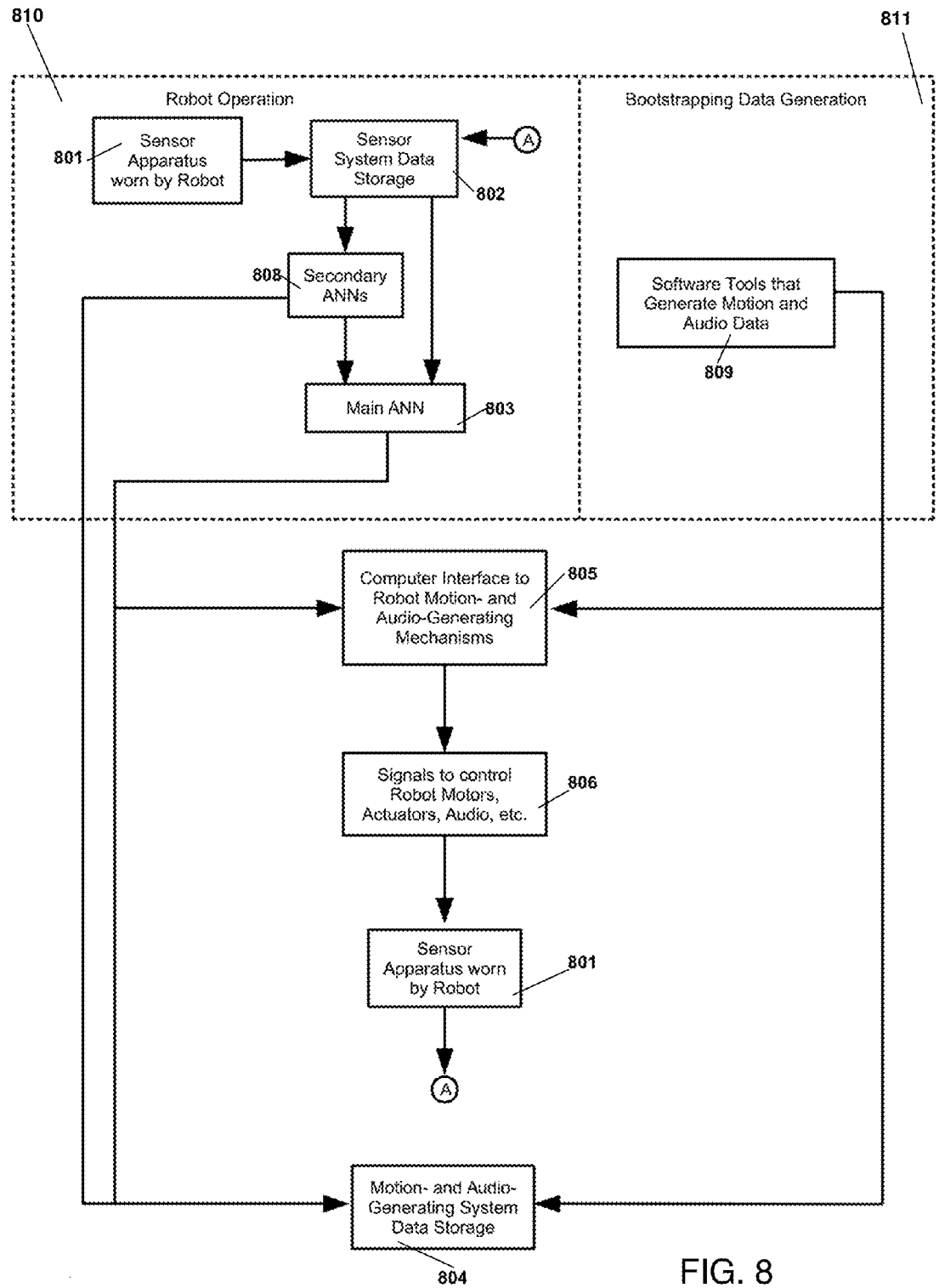
FIG. 8 illustrates overall flow of sensor, secondary ANN, and control signal data, according to one embodiment of the present invention.

FIG. 8 illustrates overall flow of sensor, secondary ANN, and control signal data, according to one embodiment of the present invention. As illustrated, a method for generating bootstrapping data for the initial training of the ANN is illustrated alongside the data flow during day to day robot operation in two regions enclosed by dotted rectangles, as represented by reference numerals 810 and 811. The region 810 shows the data flow during day to day robot operation. Sensor apparatus 801 generates sensor data which is put into the sensor apparatus data storage system 802, and is also fed into any secondary ANNs 808 that may be present. Secondary ANNs 808 feed their output into both the main ANN 803 and the motion- and audio-generating system data storage system 804. The main ANN 803 also receives the same data from the sensor apparatus data storage system 802 as the secondary ANNs 808, and uses the data from both 802 and 808 to produce as its outputs a set of data that encodes the signals needed to generate the next time interval of robot motion and audio, and these are sent to both the computer interface to the robot motion- and audio-generating mechanisms 805, which are in turn distributed to the various effectors and audio generating devices 806 to cause the robot to perform, as well as to the motion- and audio-generating system data storage system 804 for storage. In one embodiment, once the effector and audio signals have caused their respective effectors and audio generating devices to generate robot behavior, sensor apparatus 801 captures the behavior by means of its sensors. As illustrated, sensor apparatus 801 has been presented at two locations on the diagram for clarification, however, they are same component.

Region 811 of FIG. 8 illustrates a suite of computer software tools 809 can be used as an alternative to generate motion and audio data signals based on heuristics, formulas, manual operation by one or more human operators, edited or curated data from living subjects, or any other arbitrary strategies or criteria known to those skilled in the art, or combination thereof, in order to cause the robot to produce motion and sound. In one embodiment, software tools 809 generate desired encoded motion and audio data, and can be sent to both the computer interface to the robot motion- and audio-generating mechanisms 805 to cause the robot to perform as before, as well as to the motion- and audio-generating system data storage 804 for storage.

Computer interface 805 can, in one embodiment, distribute the encoded motion and audio data to their respective effectors 806 and can be a part of the robot itself. At any given time, only one of the two means, that is, data from ANN 803 or software tools 809, can be used to drive the robot. Thus, either the robot is operating autonomously under the control of the main ANN 803, or it is being driven directly by means of the software tools 809, but not both at once. Initially, ANN 803 is untrained. A collection of training data needs to be created, in which the inputs are the sensor data from 801 and the outputs are the signals to be fed into computer interface 805. However, since there is no trained ANN to generate the signals to feed into 805, sensor apparatus 801 has no behavior to capture. Thus, by creating a set of software tools 809 to generate the data for 805 a robot wearing a sensor apparatus 801 can be systematically driven and both the effector signals and the sensor data that result from them can be collected and used to create training data for the ANN.

Figure 9:
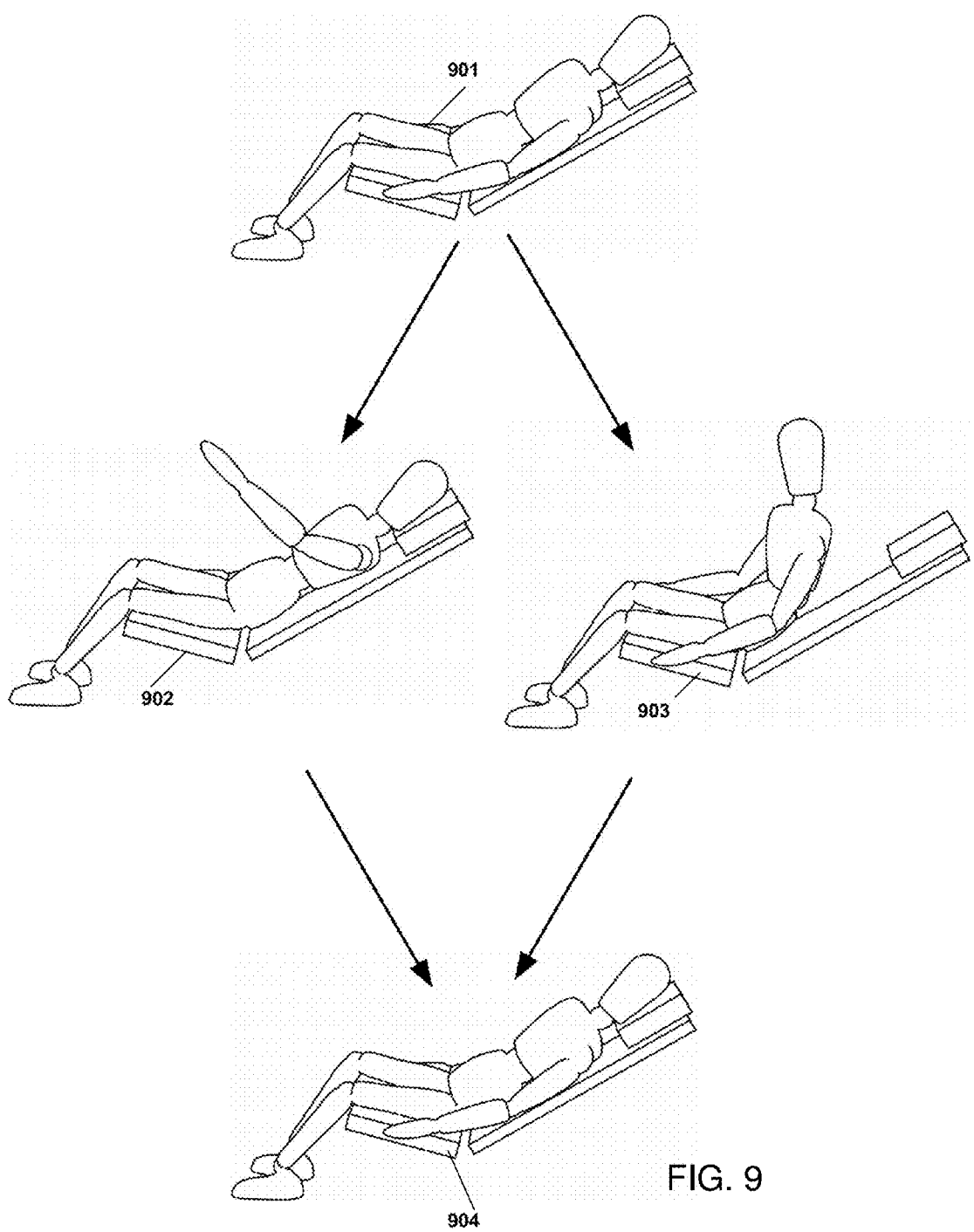
FIG. 9 illustrates exemplary actions that can be carried out in parallel by both living subjects and autonomous mobile robots under software control in order to generate initial bootstrapping training data for the primary ANN.

FIG. 9 illustrates exemplary actions that can be carried out in parallel by both living subjects and autonomous mobile robots under software control in order to generate initial bootstrapping training data for the primary ANN. As illustrated, 901 can be a living subject or a robot lying on a reclining chair. In both cases, the living subject and/or the robot are wearing sensor apparatus 801 which captures their behavior by means of its sensors. They are also capturing audio and video of their surroundings. In both cases, a technician gives verbal commands, such as "raise your left arm," resulting in both the living subject and the robot adopting a pose similar to 902. In the case of a living human subject, the command is followed upon because the living subject understands the command. This is not the case for the robot. It raises its hand because after the technician gives the spoken command, that same technician or a different technician uses the robot driving software 809 to cause the robot to raise its left arm as in 902. It is intended that such robotic motion is developed and tested earlier, along with a plurality of other stock motions and vocalizations, as well as a plurality of variations of each. In one embodiment, these robot motions and vocalizations are enumerated in a catalog and each is described in sufficient detail that the living human subject can also carry them out. Another command, "lower your left arm," can be followed by the living subject and the robot (under the control of the robot driving software 809) only if the left arm is already raised. This would cause the living subject or the robot to adopt pose 904. Starting from pose 901, the commands "sit up," and then "lie back down" would cause either the living subject or the robot to first adopt pose 903, and then pose 904.

In the cases of both the living subject and the robot, a data set results which contains the effector control signals that are fed into 805, as well as the sensor data from 801 that result from those signals. The sensor data captured from the software-driven robot, can be, in one embodiment, unnatural and clearly different from the sensor data captured from the living subject, but in numerical terms, they are covering the same space in terms of both effector signals and sensor data. The effector signals from the robot driving software and their resulting sensor data are used as described in FIGS. 4 and 5 to bootstrap the main ANN with its initial ability to function:

effector signals for next time interval=$f$(sensor signals from last several time intervals)

Since sensor data is also being captured from a living subject doing exactly the same activities as the software-driven robot, the sensor data from the living subject can be fed into the bootstrapped ANN to generate effector control signals that can result in much more natural movements of the robot.

Initially, a large amount of data can be gathered from one or a plurality of software-driven robots in order for the ANN training to begin generating accurate mappings from sensor data to effector signals. Once that occurs, the data from the living subject can be fed into the robot via an interface to 802 to cause the robot to generate movements and vocalizations, and thereby generate more training data. This data, however, may include much more natural movements and vocalizations closely resembling those of the living subject. Eventually, it may no longer be necessary to generate training data using robot driving software 809, and subsequent training data may come exclusively from behavior captured from the living subject. At all times, however, in one embodiment, both the effector signals and the sensor data, regardless of their origin, may be subject to editing, curation, smoothing, and any other modifications or enhancements as are deemed necessary to improve the process.

The overall process of bootstrap training as well as the larger scale training using only living subjects can be significantly improved and accelerated by using a plurality of both living subjects and robots. The training of the ANNs is faster in proportion to the amount of ANN training data available. This will also result in more robust pattern detection within the training data and will fill in any gaps or quirks that may be present in data from specific living subjects or robots.

The techniques shown in the figures can be implemented using computer program instructions (computer code) and data stored and executed on one or more electronic systems (e.g., computer systems, etc.). Such electronic systems store and communicate (internally and/or with other electronic systems over a network) code and data using machine-readable media, such as machine-readable non-transitory storage media (e.g., magnetic disks; optical disks; random access memory; dynamic random access memory; read only memory; flash memory devices; phase-change memory). In addition, such electronic systems typically include a set of one or more processors coupled to one or more other components, such as one or more storage devices, user input/output devices (e.g., a keyboard, a touchscreen, and/or a display), and network connections. The coupling of the set of processors and other components is typically through one or more busses and bridges (also termed as bus controllers). The storage device and signals carrying the network traffic respectively represent one or more machine-readable storage media and machine-readable communication media. Thus, the storage device of a given electronic device typically stores code and/or data for execution on the set of one or more processors of that electronic device.

It should be apparent from this description that aspects of the present invention may be embodied, at least in part, in software. That is, the techniques may be carried out in a computer system or other computer system in response to its processor, such as a microprocessor, executing sequences of instructions contained in memory, such as a ROM, DRAM, mass storage, or a remote storage device. In various embodiments, hardware circuitry may be used in combination with software instructions to implement the present invention. Thus, the techniques are not limited to any specific combination of hardware circuitry and software nor to any particular source for the instructions executed by the computer system. In addition, throughout this description, various functions and operations are described as being performed by or caused by software code to simplify description. However, those skilled in the art will recognize what is meant by such expressions is that the functions result from execution of the code by a processor.

Figure 10:
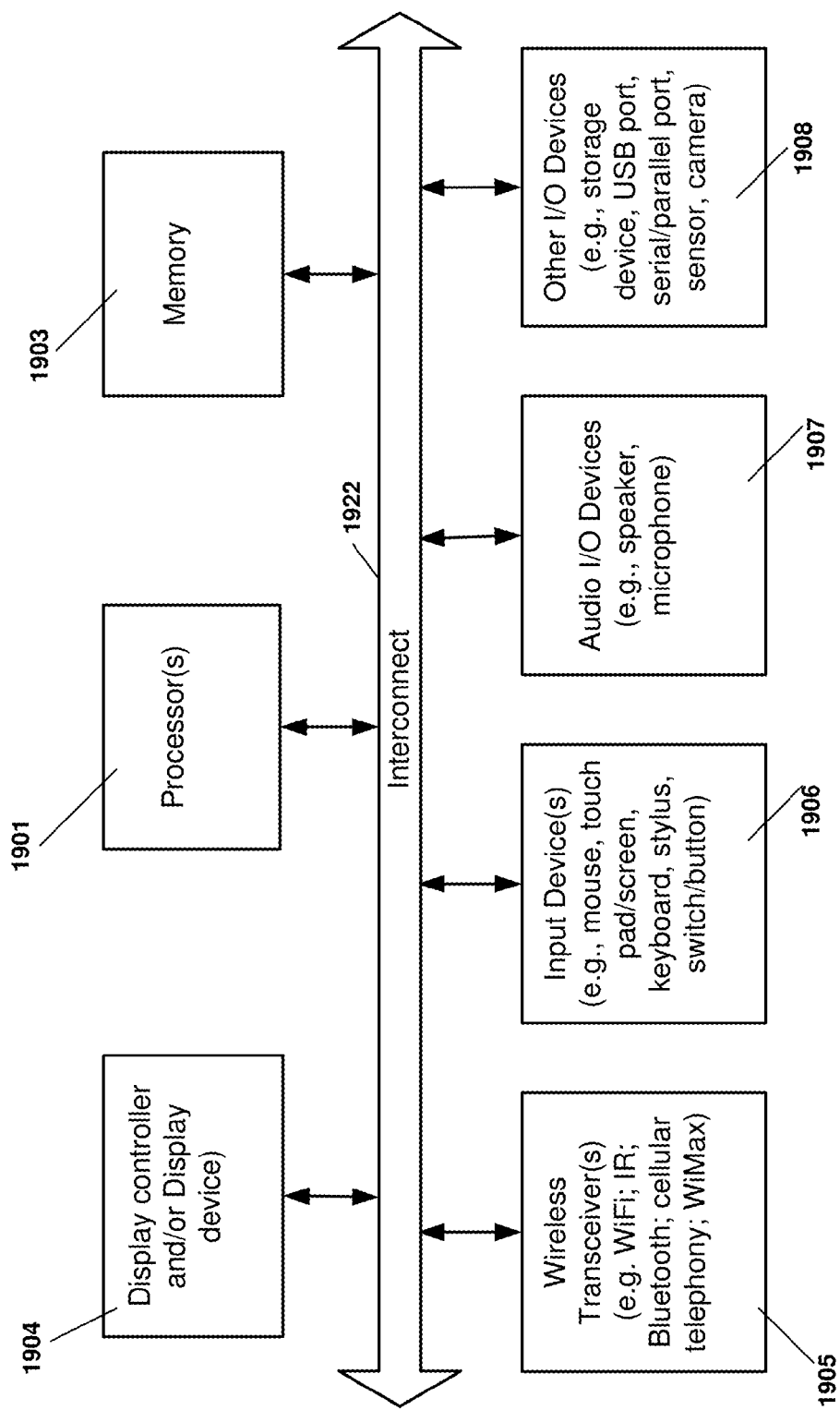
FIG. 10 is a block diagram illustrating a data processing system such as a computing system which may be used with one embodiment of the invention.

FIG. 10 is a block diagram illustrating a data processing system such as a computing system 1900 which may be used with one embodiment of the invention. For example, system 1900 may be implemented as part of an autonomous robot as described herein In one embodiment, system 1900 may represent at least a part of primary ANN 803 or secondary ANN 805. System 1900 may have a distributed architecture having dispersed units coupled through a network, or all of its components may be integrated into a single unit.

For example, computing system 1900 may represents any of data processing systems described above performing any of the processes or methods described above. System 1900 can include many different components. These components can be implemented as integrated circuits (ICs), portions thereof, discrete electronic devices, or other modules adapted to a circuit board such as a motherboard or add-in card of the computer system, or as components otherwise incorporated within a chassis of the computer system. Note also that system 1900 is intended to show a high level view of many components of the computer system. However, it is to be understood that additional or fewer components may be present in certain implementations and furthermore, different arrangement of the components shown may occur in other implementations. System 1900 may represent a desktop, a laptop, a tablet, a server, a mobile phone, a programmable logic controller, a personal digital assistant (PDA), a personal communicator, a network router or hub, a wireless access point (AP) or repeater, a set-top box, or a combination thereof.

In one embodiment, system 1900 includes processor 1901, memory 1903, and devices 1905-1908 via a bus or an interconnect 1922. Processor 1901 may represent a single processor or multiple processors with a single processor core or multiple processor cores included therein. Processor 1901 may represent one or more general-purpose processors such as a microprocessor, a central processing unit (CPU), or the like. More particularly, processor 1901 may be a complex instruction set computing (CISC) microprocessor, reduced instruction set computing (RISC) microprocessor, very long instruction word (VLIW) microprocessor, or processor implementing other instruction sets, or processors implementing a combination of instruction sets. Processor 1901 may also be one or more special-purpose processors such as an application specific integrated circuit (ASIC), a cellular or baseband processor, a field programmable gate array (FPGA), a digital signal processor (DSP), a network processor, a graphics processor, a network processor, a communications processor, a cryptographic processor, a co-processor, an embedded processor, or any other type of logic capable of processing instructions.

Processor 1901, which may be a low power multi-core processor socket such as an ultra-low voltage processor, may act as a main processing unit and central hub for communication with the various components of the system. Such processor can be implemented as a system on chip (SoC). In one embodiment, processor 1901 may be an Intel® Architecture Core™-based processor such as an i3, i5, i19 or another such processor available from Intel Corporation, Santa Clara, Calif. In one embodiment, processor 1901 may be an Nvidia® Graphical Processing Unit (GPU) or another such processor available from Nvidia Corporation, Santa Clara, Calif. However, other low power processors such as available from Advanced Micro Devices, Inc. (AMD) of Sunnyvale, Calif., an ARM-based design from ARM Holdings, Ltd. or a MIPS-based design from MIPS Technologies, Inc. of Sunnyvale, Calif., or their licensees or adopters may instead be present in other embodiments.

Processor 1901 is configured to execute instructions for performing the operations and methods discussed herein. System 1900 further includes a graphics interface that communicates with graphics subsystem 1904, which may include a display controller and/or a display device. Processor 1901 may communicate with memory 1903, which in an embodiment can be implemented via multiple memory devices to provide for a given amount of system memory. As examples, the memory can be in accordance with a Joint Electron Devices Engineering Council (JEDEC) low power double data rate (LPDDR)-based design such as the current LPDDR2 standard according to JEDEC JESD 207-2E (published April 2007), or a next generation LPDDR standard to be referred to as LPDDR3 that will offer extensions to LPDDR2 to increase bandwidth. As examples, 2/4/8 gigabytes (GB) of system memory may be present and can be coupled to processor 1901 via one or more memory interconnects. In various implementations the individual memory devices can be of different package types such as single die package (SDP), dual die package (DDP) or quad die package (QDP). These devices can in some embodiments be directly soldered onto a motherboard to provide a lower profile solution, while in other embodiments the devices can be configured as one or more memory modules that in turn can couple to the motherboard by a given connector.

Memory 1903 can be a machine readable non-transitory storage medium such as one or more volatile storage (or memory) devices such as random access memory (RAM), dynamic RAM (DRAM), synchronous DRAM (SDRAM), static RAM (SRAM), or other types of storage devices such as hard drives and flash memory. Memory 1903 may store information including sequences of executable program instructions that are executed by processor 1901, or any other device. For example, executable code and/or data of a variety of operating systems, device drivers, firmware (e.g., input output basic system or BIOS), and/or applications can be loaded in memory 1903 and executed by processor 1901. An operating system can be any kind of operating systems, such as, for example, Windows® operating system from Microsoft®, Mac OS®/iOS® from Apple, Android® from Google®, Linux®, Unix®, or other real-time or embedded operating systems such as VxWorks.

System 1900 may further include IO devices such as devices 1905-1908, including wireless transceiver(s) 1905, input device(s) 1906, audio IO device(s) 19019, and other IO devices 1908. Wireless transceiver 1905 may be a WiFi transceiver, an infrared transceiver, a Bluetooth transceiver, a WiMax transceiver, a wireless cellular telephony transceiver, a satellite transceiver (e.g., a global positioning system (GPS) transceiver), or other radio frequency (RF) transceivers, network interfaces (e.g., Ethernet interfaces) or a combination thereof.

Input device(s) 1906 may include a mouse, a touch pad, a touch sensitive screen (which may be integrated with display device 1904), a pointer device such as a stylus, and/or a keyboard (e.g., physical keyboard or a virtual keyboard displayed as part of a touch sensitive screen). For example, input device 1906 may include a touch screen controller coupled to a touch screen. The touch screen and touch screen controller can, for example, detect contact and movement or break thereof using any of a plurality of touch sensitivity technologies, including but not limited to capacitive, resistive, infrared, and surface acoustic wave technologies, as well as other proximity sensor arrays or other elements for determining one or more points of contact with the touch screen.

Audio IO device 1907 may include a speaker and/or a microphone to facilitate voice-enabled functions, such as voice recognition, voice replication, digital recording, and/or telephony functions. Other optional devices 1908 may include a storage device (e.g., a hard drive, a flash memory device), universal serial bus (USB) port(s), parallel port(s), serial port(s), a printer, a network interface, a bus bridge (e.g., a PCI-PCI bridge), sensor(s) (e.g., a motion sensor such as an accelerometer, gyroscope, a magnetometer, a light sensor, compass, a proximity sensor, etc.), or a combination thereof. Optional devices 1908 may further include an imaging processing subsystem (e.g., a camera), which may include an optical sensor, such as a charged coupled device (CCD) or a complementary metal-oxide semiconductor (CMOS) optical sensor, utilized to facilitate camera functions, such as recording photographs and video clips. Certain sensors may be coupled to interconnect 1907 via a sensor hub (not shown), while other devices such as a keyboard or thermal sensor may be controlled by an embedded controller (not shown), dependent upon the specific configuration or design of system 1900.

To provide for persistent storage of information such as data, applications, one or more operating systems and so forth, a mass storage (not shown) may also couple to processor 1901. In various embodiments, to enable a thinner and lighter system design as well as to improve system responsiveness, this mass storage may be implemented via a solid state device (SSD). However in other embodiments, the mass storage may primarily be implemented using a hard disk drive (HDD) with a smaller amount of SSD storage to act as a SSD cache to enable non-volatile storage of context state and other such information during power down events so that a fast power up can occur on RE-initiation of system activities. Also a flash device may be coupled to processor 1901, e.g., via a serial peripheral interface (SPI). This flash device may provide for non-volatile storage of system software, including a basic input/output software (BIOS) as well as other firmware of the system.

Note that while system 1900 is illustrated with various components of a data processing system, it is not intended to represent any particular architecture or manner of interconnecting the components; as such details are not germane to embodiments of the present invention. It will also be appreciated that network computers, handheld computers, mobile phones, and other data processing systems which have fewer components or perhaps more components may also be used with embodiments of the invention.

Thus, methods, apparatuses, and computer readable medium to train an autonomous robot using data collected from a living subject are described herein. Although the present invention has been described with reference to specific exemplary embodiments, it will be evident that various modifications and changes may be made to these embodiments without departing from the broader spirit and scope of the invention as set forth in the claims. Accordingly, the specification and drawings are to be regarded in an illustrative rather than a restrictive sense.

The invention claimed is:
1. An autonomous robot system comprising:
   a robot comprising a robotic skeleton designed to simulate similar actions as performed by a living subject;

a first set of sensors, coupled to the robotic skeleton, wherein the first set of sensors periodically gathering a first set of sensor data from the first set of sensors to capture motions of the robotic skeleton wherein motions of the robotic skeleton are resultant to control signals received by effectors present near or on the robotic skeleton; and a processing system coupled to the robot, the processing system configured to:
receive a second set of sensor data, the second set of sensor data generated from a sensor apparatus worn by the living subject,
process the second set of sensor data to transmit control signals to the effectors, wherein the control signals move the effectors to simulate actions performed by the living subject,
gather the first set of sensor data based on movement of the effectors, wherein the first set of sensor data generated by the effectors is substantially similar to the second set of sensor data generated from the sensor apparatus worn by the living subject, and
iteratively, perform a predictive analysis, on the first set of sensor data, to learn a capability of generating actions that are spontaneous and adaptive to an immediate environment of the robot, as well as its ongoing interactions with living or inanimate elements that surround it, wherein the processing system further receives and processes sensor data resulting from the spontaneous and adaptive actions of the robot.

2. The system of claim 1, wherein the control signals transmitted to the effectors, for a next time interval, can be represented by a conversion function represented by:

$$y=f(x)$$

wherein y represents a vector containing all signals that need to be sent to the effectors of the robot or audio generation devices in the next time interval to make the robot simulate similar actions as performed by the living subject, and x represents a vector that includes sensor readings that are produced at any given moment by the sensor apparatus, and wherein $f(\ )$ represents a machine learning algorithm function that can receive sensor data and perform computations on the sensor data to yield the control signals to send to the effectors of the robot during the next time interval.

3. The system of claim 1, wherein the predictive analysis is derived from at least a first neural network that uses layers of non-linear hidden units between its inputs and its outputs.

4. The system of claim 3, wherein each unit is assigned a weight during an initial training stage.

5. The system of claim 4, wherein during a learning stage the robot adapts the weight on incoming connections of hidden units to learn feature detectors that enable it to predict a correct output when given an input vector.

6. The system of claim 1, wherein the predictive analysis is derived from at least a first and second neural network, wherein the at least first neural network receives a feed from the first set of sensor data and wherein at least the second neural network receives a feed related to the immediate environment of the robot.

7. The system of claim 1, wherein the robotic skeleton is at least partly formed using universal joint segments.

8. A method to train an autonomous robot using data gathered from a living subject comprising:
receiving a first set of sensor data, by a processing system coupled to the autonomous robot, the first set of sensor data received from a sensor apparatus, wherein the sensor apparatus periodically gathers the first set of sensor data from the living subject;
processing the first set of sensor data and transmitting control signals to effectors of the autonomous robot to simulate actions performed by the living subject; and
iteratively, performing a predictive analysis to learn a capability of generating actions that are spontaneous and adaptive to an immediate environment of the autonomous robot, as well as its ongoing interactions with living or inanimate elements that surround it, wherein the processing system further receives and processes a second set of sensor data resulting from the spontaneous and adaptive actions of the autonomous robot;
wherein the autonomous robot includes a robotic skeleton to simulate similar actions as performed by the living subject, wherein motions of the robotic skeleton are resultant to control signals received by the effectors of the autonomous robot, the effectors present near or on the robotic skeleton.

9. The method of claim 8, wherein the control signals transmitted to the effectors, for a next time interval, can be represented by a conversion function represented by:

$$y=f(x)$$

wherein y represents a vector containing all signals that need to be sent to the effectors of the autonomous robot or audio generation devices in the next time interval to make the autonomous robot simulate similar actions as performed by the living subject, and x represents a vector that includes sensor readings that are produced at any given moment by the sensor apparatus, and wherein $f(\ )$ represents a machine learning algorithm function that can receive sensor data and perform computations on the sensor data to yield the control signals to send to the effectors of the autonomous robot during the next time interval.

10. The method of claim 8, wherein the predictive analysis is derived from at least a first neural network that uses layers of non-linear hidden units between its inputs and its outputs.

11. The method of claim 10, wherein each unit is assigned a weight during an initial training stage.

12. The method of claim 11, wherein during a learning stage the autonomous robot adapts the weight on incoming connections of hidden units to learn feature detectors that enable it to predict a correct output when given an input vector.

13. The method of claim 8, wherein the predictive analysis is derived from at least a first and second neural network, wherein the at least first neural network receives a feed from the second set of sensor data and wherein at least the second neural network receives a feed related to the immediate environment of the autonomous robot.

14. The method of claim 8, wherein the robotic skeleton is at least partly formed using universal joint segments.

15. A non-transitory computer readable medium comprising instructions which when executed by a processing system coupled to an autonomous robot performs a method to train the autonomous robot using data gathered from a living subject, the method comprising:
receiving a first set of sensor data, the first set of sensor data received from a sensor apparatus, wherein the sensor apparatus periodically gathers the first set of sensor data from the living subject;

processing the first set of sensor data and transmitting control signals to effectors of the autonomous robot to simulate actions performed by the living subject; and iteratively, performing a predictive analysis to learn a capability of generating actions that are spontaneous and adaptive to an immediate environment of the autonomous robot, as well as its ongoing interactions with living or inanimate elements that surround it, wherein the processing system further receives and processes a second set of sensor data resulting from the spontaneous and adaptive actions of the autonomous robot;

wherein the autonomous robot includes a robotic skeleton to simulate similar actions as performed by a living subject, wherein motions of the robotic skeleton are resultant to control signals received by the effectors of the autonomous robot, the effectors present near or on the robotic skeleton.

16. The non-transitory computer readable medium of claim 15, wherein the control signals transmitted to the effectors, for a next time interval, can be represented by a conversion function represented by:

$$y = f(x)$$

wherein y represents a vector containing all signals that need to be sent to the effectors of the autonomous robot or audio generation devices in the next time interval to make the autonomous robot simulate similar movements as performed by the living subject, and x represents a vector that includes sensor readings that are produced at any given moment by the sensor apparatus, and wherein $f(\ )$ represents a machine learning algorithm function that can receive sensor data and perform computations on the sensor data to yield the control signals to send to the effectors of the autonomous robot during the next time interval.

17. The non-transitory computer readable medium of claim 15, wherein the predictive analysis is derived from at least a first neural network that uses layers of non-linear hidden units between its inputs and its outputs.

18. The non-transitory computer readable medium of claim 17, wherein each unit is assigned a weight during an initial training stage.

19. The non-transitory computer readable medium of claim 18, wherein during a learning stage the autonomous robot adapts the weight on incoming connections of hidden units to learn feature detectors that enable it to predict a correct output when given an input vector.

20. The non-transitory computer readable medium of claim 15, wherein the predictive analysis is derived from at least a first and second neural network, wherein the at least first neural network receives a feed from the second set of sensor data and wherein at least the second neural network receives a feed related to the immediate environment of the autonomous robot.

* * * * *